US006447807B1

(12) United States Patent
Clouatre et al.

(10) Patent No.: US 6,447,807 B1
(45) Date of Patent: Sep. 10, 2002

(54) POTASSIUM (-)-HYDROXYCITRIC ACID METHODS FOR PHARMACEUTICAL PREPARATIONS FOR STABLE AND CONTROLLED DELIVERY

(76) Inventors: Dallas L. Clouatre, 275 Willow Rd., Menlo Park, CA (US) 94025; James M. Dunn, 3236 Hinsdale Pl., Littleton, CO (US) 80112

( * ) Notice: Subject to any disclaimer, the term of this patent is extended or adjusted under 35 U.S.C. 154(b) by 0 days.

(21) Appl. No.: 09/661,665

(22) Filed: Sep. 14, 2000

Related U.S. Application Data
(60) Provisional application No. 60/153,920, filed on Sep. 14, 1999.

(51) Int. Cl.⁷ .......................... A61K 9/16; A61K 9/50; A61K 47/00; A61K 9/22; A61K 9/00
(52) U.S. Cl. .................. 424/494; 424/400; 424/439; 424/441; 424/468; 424/499
(58) Field of Search ................ 424/494, 400, 424/439, 441, 468, 499

(56) References Cited

U.S. PATENT DOCUMENTS

| | | | |
|---|---|---|---|
| 3,764,692 A | 10/1973 | Lowenstein | 424/279 |
| 5,536,516 A | 7/1996 | Moffett et al. | 426/271 |
| 5,626,849 A | 5/1997 | Hastings et al. | 424/195.1 |
| 5,783,603 A | 7/1998 | Majeed et al. | 514/574 |
| 5,914,326 A | 6/1999 | McCarty et al. | 514/188 |

OTHER PUBLICATIONS

Clouatre, Dallas and Michael E. Rosenbaum. The Diet and Health Benefits of HCA (Hydroxicitric Acid). (Keats Publishing, New Canaan, CT: 1994).

Rao, R. Nageswara and K.K. Sakariah. Lipid–lowering and antiobesity effect of (—)–hydroxycitric acid. Nutrition Research 8, 2 (1988) 209–212.

Drury, Heber. "Garcinia cambogia" in *The Useful Plants Of India*, 2nd Edition. (William H. Allen and Co., London: 1873) p. 220.

Publications & Information Directorate, Council of Scientific & Industrial Research. *The Useful Plants of India*. (New Delhi: Publications & Information Directorate, 1986) 229.

Lewis, Y.S. and S. Neelakantan. (—)–Hydroxycitric acid— the principle acid in the fruits of *Garcinia cambogia* Desr. *Phytochemistry* 4 (1965) 619–625.

Lewis, Y. S., Isolation and properties of hydroxycitric acid. In John M. Lowenstein, ed., vol. 13 in Methods in Enzymology, *Citric Acid Cycle* (New York: Academic Press, 1969) 613–619.

Sugden, Mary C., David I. Watts, Christopher E. Marshall and James G. McCormack. Brown–adipose–tissue lipogenesis in starvation effects of insulin and (—)hydroxycitrate. *Bioscience Reports* 2,5 (1982) 289–297.

Sullivan, Ann C. and Joseph Triscari. Metabolic regulation as a control for lipid disorders. I. Influence of (—)–hydroxycitrate on experimentally induced obesity in the rodent. *The American Journal of Clinical Nutrition* 30, 5 (May 1977) 767–776.

Heymsfield, Steven B, et al. *Garcinia cambogia* (hydroxycitric acid) as a potential antiobesity agent. *JAMA* 280, 18 (1998) 1596–1600; also especially, Letters, *JAMA* 282 (1999) 235.

*Primary Examiner*—Thurman K. Page
*Assistant Examiner*—Blessing Fubara

(57) ABSTRACT

A method for making the potassium and sodium salts of (–)-hydroxycitric acid and mixtures thereof workable, non-hygroscopic and non-reactive in acidic media by encasement in hydrophobic and acidophobic polymers. The calcium and magnesium salts of (–)-hydroxycitric acid likewise can be rendered nonreactive in acidic media. The resulting products are suitable for tableting, encapsulation and use in other dry media for weight loss, appetite suppression, improvements in fat metabolism and postprandial lipemia and other pharmaceutical purposes. Further, the products of this invention can be made nonreactive as components of acidic liquid drink mixes and snack bars and can be used in the production of controlled release administration formats.

12 Claims, No Drawings

POTASSIUM (-)-HYDROXYCITRIC ACID METHODS FOR PHARMACEUTICAL PREPARATIONS FOR STABLE AND CONTROLLED DELIVERY

PROVISIONAL PATENT APPLICATION FILING

This application is entitled to the benefit of Provisional patent application Ser. No. 60/153,920 filed Sep. 14, 1999, "Potassium (-)-Hydroxycitric Acid Methods For Pharmaceutical Preparations For Stable And Controlled Delivery"

RELATED PROVISIONAL PATENT APPLICATION FILINGS

Ser. No. 60/153,923

Date: Sep. 14, 1999

Methods And Pharmaceutical Preparations For Treating Obesity with (-)-Hydroxycitric Acid Ser. No. 60/153,924

Date: Sep. 14, 1999

Methods And Pharmaceutical Preparations For Treating Postprandial Lipemia With (-)-Hydroxycitric Acid

BACKGROUND OF THE INVENTION

1. Field of the Invention

The invention is directed toward a novel process by which the salts of (-)-hydroxycitric acid, either potassium (-)-hydroxycitrate, the preferred salt of (-)-hydroxycitric acid, or, alternatively, sodium (-)-hydroxycitrate, can be rendered suitable for tableting, encapsulation and use in other dry media for weight loss and other pharmaceutical purposes. Furthermore, the product of this invention can be made nonreactive as a part of acidic drink mixes and acidic snack bars. This invention is further directed toward the production of controlled release versions of potassium or sodium (-)-hydroxycitrate which can be used to provide multi-hour controlled release of the compound.

2. Description of Prior Art (-)-Hydroxycitric acid (abbreviated herein as HCA) a naturally-occurring substance found chiefly in fruits of the species of Garcinia, and several synthetic derivatives of citric acid have been investigated extensively in regard to their ability to inhibit the production of fatty acids from carbohydrates, to suppress appetite, and to inhibit weight gain. (Sullivan, A. C., et al., American Journal of Clinical Nutrition 1977;30:767.) Numerous other benefits have been attributed to the use of HCA, including, but not limited to an increase in the metabolism of fat stores for energy and an increase in thermogenesis (the metabolism of energy sources to produce body heat in an otherwise wasteful cycle). One commonly offered explanation for the effects of HCA is that this compound inhibits the actions of cytoplasmic (cytosolic) ATP:citrate lyase. (D. Clouatre and M. E. Rosenbaum, The Diet and Health Benefits of HCA (Hydroxicitric Acid), 1994.) Weight loss benefits are ascribed to HCA, its salts and its lactone in U.S. Pat. No. 3,764,692 granted to John M. Lowenstein in 1973. Lowenstein described a variety of possible pharmaceutical salts of HCA based upon alkali metals, e.g., potassium and sodium, and alkaline earth metals, e.g., calcium,. The production of the potassium salt of HCA had been described in the scientific literature previous to Lowenstein's patent, but not in regard to its weight-loss properties. Research into HCA by scientists at the pharmaceutical firm of Hoffman-La Roche revealed that the lactone form of HCA is far less effective than is the sodium salt of HCA for weight loss purposes, in part because the lactone form lacks the proper affinity for the receptor which is the target of the actions of HCA. However, the sodium salt has disadvantages for long-term administration, both because sodium possesses no positive metabolic effects with regard to obesity and because sodium has potential hypertensive actions as well as other drawbacks. Potassium, as a ligand for HCA, does not possess the disadvantages associated with sodium. Moreover, the absorption of the potassium salt of HCA is considered to be superior to that of the sodium salt owing to the greater rate of uptake of potassium in relation to sodium in most tissues.

Free (-)-hydroxycitric acid, calcium, magnesium and potassium salts of HCA and poorly characterized mixtures of two or more of these minerals, usually substantially contaminated with sodium, currently exist on the American market. Most of the HCA sold consists of calcium salts of varying purity. Aside from the potassium salt, all of these HCA forms suffer from problems in assimilation, a fact attested to by poor performance in controlled weight loss trials. For instance, the free acid form of (-)-hydroxycitric acid is extremely ionic and does not pass readily through the gut membranes. Free HCA has several further disadvantages. It undergoes rapid lacontonization, and, again, the lactone form has no appreciable physiological activity. Indeed, inclusion of any of the currently available mineral salts of HCA in a prepared beverage of acidic pH will lead to the development of the HCA lactone over time. The free acid form, moreover, has a tendency to be bound up and made unavailable to the body by soluble and insoluble fibers as well as by many other compounds. Likewise the potassium and sodium salts, if placed even only briefly in acidic or flavored beverages, typically will undergo color change or exhibit other signs of having undergone chemical interaction with the contents of the beverage. Thus although a patent exists for the use of free (-)-hydroxycitric acid concentrate in food products (U.S. Pat. No. 5,536,516), the art taught therein offers no particular advantages for weight loss nor for other medicinal purposes.

The calcium and magnesium salts of HCA are poorly absorbed from the gastrointestinal tract because they are poorly soluble in aqueous media and because both of these minerals are saponified by bile acids and fats in the gut and/or are bound up by soluble and insoluble fibers or other substances in the diet or secreted during digestion. Some of these problems have been pointed out by medical researchers and admitted in print by at least one primary manufacturer of HCA products. (Heymsfield, Steven B, et al. JAMA 1998;280(18):1596–1600; Letters, JAMA 1999;282:235.) Moreover, there is no evidence that merely making calcium and magnesium salts of HCA more soluble, such as can be accomplished by adding small amounts of potassium and/or sodium and/or lactone, will solve the problem of assimilation. HCA is known to have three separate binding points, and simple chemical experimentation quickly shows that divalent ions, such as those of calcium and magnesium, cannot be readily separated by the application of other acids, such as human gastric acid, from the HCA once these minerals have been reacted with it. The action of stomach acid, however, may free one of the two valences of calcium or magnesium for attachment to fats, bile acids, gums, fibers, pectins, and so forth and so on, which is an undesirable outcome. For weight loss and other purposes, a minimally effective amount of HCA derived from its calcium salt requires the administration of between 12 and 15 grams of a 50% material, and this amount of calcium (−)-hydroxycitrate will lead to undesirably elevated levels of binding and excretion of other dietary minerals, such as zinc, aside from presenting difficulties in administration. Animal trials (not published) have further demonstrated that in order for the potassium salt to be maximally effective, the ligand must be fully bound to the HCA with only minimal amounts of contaminants, including other minerals or fibers or sugars. Hence the calcium and magnesium salts, either alone or in the form of various mixtures together or in combination with the potassium and sodium salts, are not preferred delivery forms for HCA.

The preferred salt of HCA for pharmaceutical use is potassium (−)-hydroxycitrate (abbreviated herein as KHCA). The mineral potassium is fully soluble, as is its HCA salt, and is known to possess cell membrane permeability which is 100 times greater than that possessed by sodium. However, the potassium salt of HCA, as is also true of the sodium salt, is extremely hygroscopic and thus not suitable under normal circumstances for the production of dry delivery forms. In drawing moisture to itself, KHCA will also tend to bind to available binding sites of compounds in its immediate environment, and this action often later will markedly impede the assimilation of KHCA from the gut. KHCA is also not suitable for liquid delivery forms inasmuch as KHCA in solution, will slowly lactonize to an equilibrium which is dependent upon the pH. One recent patent (U.S. Pat. No. 5,783,603) does teach a technique for the production of KHCA, but this material is nonhygroscopic only under the conditions mentioned specifically in that patent, to wit, "milling, sifting, blending and packing said dried precipitate under nitrogen to obtain said potassium hydroxycitric acid [sic] composition." If left in the open air outside of a humidity-controlled environment, the KHCA produced according to that patented method will begin to absorb moisture within a few minutes. Except as a very minor ingredient, it cannot be used as a component of dry pharmaceutical or nutriceutical preparations. Hence, no prior art teaches the production of the relatively pure potassium salt of (−)-hydroxycitric acid in a form which is workable under those conditions necessary for tableting, encapsulation, the production of controlled release vehicles nor incorporation into dry powders, such as dry meal replacement mixes. No prior art teaches a method of including potassium or other forms of HCA in liquid media without lactonization and no prior art teaches a method by which KHCA may be delivered under controlled release. Likewise, no prior art teaches the above with regard to sodium (−)-hydroxycitrate.

Furthermore, the lack of a method of producing a controlled release form of HCA, regardless of the salt used, has led to a problem in the delivery of the drug. Tests performed to establish the appetite-suppressing effects of HCA found that a single large oral dose or two divided oral doses totaling one fourth the size of the single dose resulted in a 10% or greater reduction in food consumption in experimental animals fed a high-sugar diet. This result continued over many weeks with the chronic ingestion of HCA. The requirement for at least two divided doses of HCA for efficacy is the only thoroughly established procedure to date.

Giving HCA as multiple doses, as is true of any drug, is inconvenient and is not supported by good patient compliance. Multiple doses given in the form of any of the current salts is also wasteful in that any material delivered to the body which is above the baseline or threshold necessary to produce benefits is simply an excess which is excreted. Controlled release of HCA would avoid both excess and waste, on the one one, and gaps in coverage, on the other hand. Controlled release makes it possible to simplify the dosage schedule to one daily administration. Moreover, it is to be expected that a smaller amount of HCA delivered by controlled release will provide benefits which are superior to those found with a larger amount of HCA supplied after a normal fashion in at least two dosages.

SUMMARY OF THE INVENTION

The present invention resolves the problems described above with regard to the use of the potassium and sodium salts of (−)-hydroxycitric acid. The principle is provided by which the hygroscopic salts of (−)-hydroxycitric acid in their relatively pure and active forms, including especially the potassium salt, but also including the sodium salt, are rendered non-hygroscopic and stable (that is, not prone to lactonization, not readily subject to attachment to ligands which inhibit absorption or lead to excretion, and so forth as described previously) such that these HCA salts might be included in dry delivery formats, liquid delivery and in controlled-release vehicles. Moreover, the nonhygroscopic salts of (−)-hydroxycitric acid may also be protected against acid degradation, lactonization and undesirable ligand binding when exposed to acidic environments or other challenging conditions.

Objects and Advantages

The potassium salt of (−)-hydroxycitric acid is the most efficacious form of HCA to be used for human weight loss and for other pharmaceutical and/or neutraceutical purposes, followed secondarily for these purposes by the sodium salt. The potassium and the sodium salts of HCA present very similar difficulties in handling and manipulation. Potassium (−)-hydroxycitrate is extremely hygroscopic and tends to bind with water in the open air to form a non-palatable paste not suitable for use in tablets, capsules or powders. This material can be admixed with orange juice or water, but requires vacuum pouch sealing under a humidity-controlled atmosphere and is inconvenient for the patient to use. KHCA, moreover, is reactive with a large number of compounds (tannins, gums, fibers, pectins, and so forth) are thereby readily suffers large losses in pharmacological availability.

Using acceptable, yet novel pharmaceutical art forms for this product, the inventors have been successful in granulating the potassium salt form of (−)-hydroxycitric acid extract into a fine coated powder which is acid resistant and which retards water inclusion into the material. This has been accomplished by coating the particulate material with an acid retardant film and then exposing the product to a high heat environment which produces a dry (<3% moisture) white powder which can be compressed into a tablet, used to fill a hard gelatin capsule or admixed into a viscous flavored drink or into a meal replacement or acidic snack bars. By using an acid retardant coating, we prevent exposure to possibly binding compounds prior to ingestion and also in the stomach and upper gastrointestinal tract above to the point at which the KHCA can be absorbed. We thus allow for the optimum absorption of the KHCA in the small intestine. The polymer film acts as a water barrier which allows for various forms of pharmaceutically acceptable preparations to be prepared from the raw material. The method described applies to the potassium salt of (−)-hydroxycitric acid; with minor revisions it can be applied to the sodium salt, to mixtures or combinations of the two salts, and to combinations of these salts in which calcium or magnesium (−)-hydroxycitrate are additions. The treated material produced according to our discovery can further be used to produced controlled release dosage forms with their many inherent biologic advantages, including the possibility of reducing intake of the compound to one daily administration.

DESCRIPTION OF THE PREFERRED EMBODIMENTS

The raw material is the potassium salt of (−)-hydroxycitric acid which has been produced from the aqueous extract of *Garcinia cambogia*, other Garcinia species or by synthesis. In hydrated form, it is a viscous deep brown. It has a earthy smell and contains approximately 6 parts by weight of solids per liter of fluid. The novel concept is to encase the potassium salt of (−)-hydroxycitric acid with an acidophobic and hydrophobic polymer after driving off the water from the raw material. The polymer employed will not bind to the ligand sites of the raw material. This procedure results in a material which is resistant to water and acid media. Moreover, by so coating the raw material, it becomes possible to easily work with it for the production of pharmaceutical formulations of various types and nature, to form it into edible bars, drinks, and other marketable forms of the basic substance. In addition, when the treated material is ingested, it resists degradation by the acid of the upper intestinal tract. Treatment allows for a prolonged release time in the more basic pH of the small intestine, and this, in turn, allows for a slow and steady diffusion of the active ingredient across the gut wall.

Methods Of Preparation

In essence the potassium salt of (−)-hydroxycitric acid is made aqueous by the addition of deionized water by bringing the volume to 5 L of water. In a separate container 1 L of deionized water is ammoniated with approximately 1,000 mL of 28% ACS ammonium hydroxide and stirred. Into the KHCA is added 1 kg of maltodextrin and the mixture of maltodextrin and KHCA is stirred with a medium propeller mixer. Into the 1 L of ammonium hydroxide is added 5 gm of cellulose acetate phthalate (CAP), which is the polymer for encasement. The CAP is then slowly poured into the blending KHCA and maltodextrin; deionized water is added until the weights/water are 24–25%. This thoroughly admixed solution is then passed into a spray dry chamber at 265° C. using a Watson Marlow pump and a flow rate at 1–2 L/minute. The powder is an off white dusk color and is collected in the collection bowl until all the fluid has been passed through the pump. The powder contains about 35% of KHCA by weight. When left in an open plastic boat there is no evidence of hygroscopic interaction after 1 week with a relative humidity of 70%. The powder showed no signs of degradation or discoloration after this time. To allow the powder to flow without sticking, magnesium stearate is added for capsule filling or tableting. With the proper revisions by one skilled in the art, this procedure can be applied readily to potassium, sodium or other salts of (−)-hydroxycitrate to be processed via fluid bed dryer.

The following are examples of encapsulation and tableting which may be performed with the KHCA powder produced from this novel procedure. With very little modification, the same examples can be applied to a powder produced from sodium (−)-hydroxycitrate by the novel procedure.

EXAMPLE 1

| | Ingredient | Weight | Percent |
|---|---|---|---|
| 1. | KHCA Powder (35% KHCA) | 1.000 gm | 54.05% |
| 2. | Cellulose Acetate Phthalate | 0.500 gm | 27.02% |
| 3. | Calcium Sulfate | 0.300 gm | 16.22% |
| 4. | Talc | 0.030 gm | 1.63% |
| 5. | Magnesium Stearate | 0.020 gm | 1.08% |
| | Total | 1.850 gm | 100.00% |

The powder from Example 1 can be used to compress tablets weighing 1,000 to 1,500 mg which would contain from would contain from 540 to 818 mg of the prepared KHCA powder. Considering that the starting material is only 35% active, the amount of KHCA per tablet would be 189–287 mg. These tablets will not dissolve in the acid media of the stomach and will start a gradually release of the drug product once they arrive in the more pH neutral media of the 2nd part of the small intestine. Additionally these tablets can be over coated with a clear film to protect them from any random damage, but this will not affect their dissolution rate.

EXAMPLE 2

| | Ingredient | Weight | Percent |
|---|---|---|---|
| 1. | KHCA Powder (35%) | 1.000 gm | 81.97% |
| 2. | Anhydrous Lactose | 0.200 gm | 16.39% |
| 3. | Magnesium Stearate | 0.020 gm | 1.64% |
| | Total | 1.220 gm | 100.00% |

The KHCA powder is blended with anhydrous lactose and magnesium sterate for 3 minutes per kilogram. The powder should have a smooth flow and easily fill an 0 capsule to a weight of 750 mg yielding about 220 mg of KHCA per capsule. The amount of KHCA can be increased by decreasing the amount of excipients to where they flow well in the encapsulating machine. Because the coating of the KHCA will prevent its destruction in the acidic environment of the stomach it may be that this formulation technology will perform in a superior manner and the amount of KHCA delivered in this fashion required for efficacy will be smaller than that which is required with the liquid or plain capsule formulations used in past clinical trials.

EXAMPLE 3

A less elegant manner of delivering the drug is in the form of a acidic shake or drink. The drink formula can be made in the following manner:

| | Ingredient | Weight | Percent |
|---|---|---|---|
| 1. | KHCA Powder (35%) | 1.000 gm | 48,78% |
| 2. | Deionized Water | 0.750 gm (750 mL) | 36.58% |
| 3. | Hydroxy-Propyl Cyclodextrin | 0.200 gm | 9.76% |
| 4. | Glycerin | 0.050 gm | 2.44% |
| 5. | Orange Flavoring | 0.050 gm | 2.44% |
| 6. | Orange Coloring | QS for Color | |
| | Total | 2.050 gm | 100.00% |

This is one example in which the cyclodextrin acts as a further chemical basket to entrap the KHCA and hold it in suspension. To thicken the solution one can add methocel power or pectin. If the use of carbopol is anticipated, it will have to be neutralized with an alkaline product inducing a higher pH and running the risk of premature rupture of the acid retardant film about the granulate. To maintain a slight acidity to the drink use citric acid or similar U.S.P. approved fruit acid.

Another method of producing a tablet is by slugging the powered material first then sizing it through a proper mesh screen and compression into a tablet.

EXAMPLE 4

|   | Ingredient | Weight | Percent |
|---|---|---|---|
| 1. | KHCA Powder (35%) | 1.000 gm | 76.9% |
| 2. | Manitol | 0.300 gm | 23.1% |
|   | Total | 1.300 gm | 100.0% |

Blend the KHCA and manitol in a blender or planetary mixer until an even and granular material is formed. Place into a rotary press or a large slugging machine and compress into a large 1–3 gm tablet with 10–15 tons of pressure. When the granulate has been slugged run it through a Fitzmill® sizing apparatus with an #063 screen. Take the sized granulate and blend with magnesium sterate 0.5%. After blending for 1 minute per kilogram place onto a rotary press and compress into tablets weighing 1000–1500 mg and a hardness of 10–15 kg.

EXAMPLE 5

Disintigration Of Capsules Made By Example 2

| Basket | Starting Weight | Ending Weight 2 Hours |
|---|---|---|
| 1 | 800 mg | 75 mg |
| 2 | 798 mg | 80 mg |
| 3 | 810 mg | 85 mg |
| 4 | 788 mg | 72 mg |
| 5 | 805 mg | 87 mg |
| 6 | 790 mg | 90 mg |
| Mean | 798.5 mg | 81.7 mg |
| Standard Deviation | 7.74 | 6.45 |

The encapsulated product showed a slow even disintegration in pH 5.6 water. In an acid media there was little or no disintegration after 4 hours.

EXAMPLE 6

|   | Ingredient | Weight | Percent | 1 Kg Batch |
|---|---|---|---|---|
| 1. | Aqueous Potassium Hydroxycitrate | 500 gm | 62.5% | 0.63 |
| 2. | Calcium Carbonate | 50 gm | 6.25% | 0.06 |
| 3. | Potassium Carbonate | 50 gm | 6.25% | 0.06 |
| 4. | Anhydrous Lactose | 150 gm | 18.75% | 0.19 |
| 5. | Cellulose Acetate Pthalate Acetate | 50 gm | 6.25% | 0.06 |
|   | Total | 800 gm | 100.00% | 100.00 |

A. Blend items 1–5 in mixing bowl until smooth and even.

B. Take the liquid and spray into spray-drying oven at 300° C. until white powder forms. When powder has formed, blend with suitable bulking agent, if necessary, and compress into 800 mg tablets with hardness of 10–15 kg. This will mean that each tablet, if starting with 62% KHCA polymer powder, will have about 31% KHCA. However, if the tablets are pressed to 1600 mg, the dose will be equal to 800×62% KHCA.

C. After pressing the granulate through the screen, make sure that it flows well and compress into oblong tablets.

D. Tablets should have a weight of 1600 mg and a hardness of 14±3 kg fracture force. When tablets are completed, check for disintegration in pH 6.8, 0.05M KH2PO4. Disintegration should occur slowly over 4–5 hours.

CONCLUSIONS (−)-Hydroxycitrate has a multitude of metabolic functions. The literature teaches that the compound induces weight loss and decreases appetite in both animals and humans. The product in the preferred form of the potassium salt and in its secondarily preferred form as a sodium salt is highly soluble and extremely hygroscopic. It can be maintained as a powder only under controlled conditions. When manipulated by normal methods, it is unstable because of its sensitivity to acids and its extremely hygroscopic nature. Without special precautions, HCA in its free acid form and in its potassium and sodium salt forms will bind to numerous other compounds and thereby to become markedly less assimilable. Hence, neither of the preferred salts of (−)-hydroxycitric acid prior to the present teaching have been fully stable or workable as capsules, tablets, powders, in beverages or prepared snacks, or in controlled release vehicles. Similarly, full potency of the compound's preferred salts can be compromised by digestive actions. Prior art teaches a method of producing a KHCA product which is stable and non-hygroscopic only so long as it is packaged under a controlled atmosphere and thereafter protected from exposure to moisture.

The present application teaches a method of spray drying the extracted material with maltodextrin and cellulose acetate phthalate. This results in a fine powder which is protected from acidic breakdown and protected from high humidity environments. Using the powder of this process, it is possible to encapsulate the material, tablet the product, to place the material into a dry drink or meal replacement powder, or to mix it into a liquid acidic drink formulation and acidic snack bars. The powder can further be manipulated to produce controlled release products. With minor revisions, one skilled in the art can use the procedures taught herein to produce acceptably stable versions of the potassium and sodium salts of (−)-hydroxycitric acid via fluid bed dryer rather than through recourse to spray drying. Likewise, one skilled in the art can use the procedures taught herein to make other non-preferred salts of (−)-hydroxycitric acid, e.g., calcium and magnesium salts and various mixtures of the known salts, amenable to stable inclusion in liquid acidic drink formulation and acidic snack bars and, likewise, protect these against the acidic environment of the upper digestive tract.

We claim:

1. A method of coating and encasing powders consisting of the salts of (−)-hydroxycitric acid in acid resistant hydrophobic polymers to produce durable and workable (−)-hydroxycitrate granulate resistant to environmental moisture, resistant to lactonization under acid environments and resistant to undesirable binding, said method comprising:

(1) obtaining a salt of (−)-hydroxycitric acid or a combination of salts of (−)-hydroxycitric acid, (2) blending said salt or combination of said salts of (−)-hydroxycitric acid with a polymer wherein the polymer is selected from the group consisting of cellulose acetate phthalate, ethyl cellulose, zein, acrylic polymers, hydroxymethylpropylmethyl cellulose phthalate, polyvinyl acetate phthalate, cellulose acetate trimalleate, acrylic polymer plasticizers, polymers of poly lactic acid, polymers of glycolic acid, and mixtures thereof, (3) the resulting encased powder product of (1) and (2) is formulated into tablets, capsules, prepared dry drink mixes, prepared liquid drinkable products and edible bars.

2. The method of claim 1, wherein said salt or combination o said salts of (−)-hydroxycitric acid is further blended with cyclodextrin.

3. The method of claim 1, wherein said salt or combination o said salts of (−)-hydroxycitric acid is spray dried or freeze dried under a vacuum or process d using a fluid bed dryer prior to formulation into tablets, capsules, prepared dry drink mixes, prepared liquid drinkable products and edible bars.

4. The method of claim 1, wherein the resulting product is a controlled release formulation.

5. The method of claim 1, wherein an effective amount of the resulting product is administered to suppress appetite in a patient in need thereof.

6. The method of claim 1, wherein an effective amount of the resulting product is administered to inhibit cytoplasmic citrate lyase in a patient in need thereof.

7. The method of claim 1, wherein an effective amount of the resulting product is administered to increase fat metabolism in a patient in need thereof.

8. The method of claim 1, wherein an effective amount of the resulting product is administered to induce weight loss in a patient in need thereof.

9. The method of claim 1, wherein an effective amount of the resulting product is administered to reduce blood lipids and postprandial lipemia in a patient in need thereof.

10. The method of claim 1, wherein the resulting product is further admixed with pharmaceutical agents and excipients and formulated into tablets, capsule, prepared dry drink mixes, prepared liquid drinkable products and edible bars.

11. The method of 2, wherein the cyclodextrin is hydroxypropyl cyclodextrin.

12. The method of 4, wherein the controlled release formulation is administered once daily.

* * * * *